United States Patent [19]
Valentine

[11] Patent Number: 5,450,145
[45] Date of Patent: Sep. 12, 1995

[54] APPARATUS AND METHOD FOR TESTING VISUAL FOCUS CONTROL

[76] Inventor: James M. Valentine, 124 Farrell Rd., Vandalia, Ohio 45377

[21] Appl. No.: 971,275

[22] Filed: Nov. 4, 1992

[51] Int. Cl.$^6$ ............................ A61B 3/02; A61B 3/10
[52] U.S. Cl. ..................... 351/243; 351/202; 351/211; 351/221; 351/237
[58] Field of Search .................. 351/200–203, 351/205, 211, 212, 222–223, 237–243, 246

[56] References Cited

U.S. PATENT DOCUMENTS

| | | | |
|---|---|---|---|
| 3,891,311 | 6/1975 | Fletcher et al. | 351/38 |
| 4,012,128 | 3/1977 | Regan | 351/243 |
| 4,294,522 | 10/1981 | Jacobs | 351/203 |
| 4,660,945 | 4/1987 | Trachtman | 351/205 |
| 4,730,917 | 3/1988 | Kauger | 351/211 |
| 4,778,268 | 10/1988 | Randle | 351/203 |
| 4,830,482 | 5/1989 | Resnikoff | 351/172 |
| 4,850,690 | 7/1989 | Parker et al. | 351/205 |
| 4,896,959 | 1/1990 | O'Brien | 351/203 |
| 4,943,151 | 7/1990 | Cushman | 351/203 |
| 5,129,717 | 7/1992 | Feinbloom | 351/158 |
| 5,129,718 | 7/1992 | Futkey et al. | 351/161 |
| 5,139,325 | 8/1992 | Oksman et al. | 351/161 |
| 5,141,301 | 8/1992 | Morstad | 351/161 |
| 5,142,411 | 8/1992 | Fiala | 359/494 |

OTHER PUBLICATIONS

Cognitive Psychology, Third Edition, by Robert L. Solso Univ. of Nevada,-Reno pp. 123–125.

Primary Examiner—Thong Q. Nguyen
Attorney, Agent, or Firm—Biebel & French

[57] ABSTRACT

An apparatus and method for testing the ability to control the focussing of an eye. A pair of images originating for apparently different distances are directed simultaneously into the eye of an observer. The observer's ability to focus selectively upon either of the images is used as an indication of tolerance to intraocular multifocal contact lenses.

8 Claims, 5 Drawing Sheets

APPARATUS AND METHOD FOR TESTING VISUAL FOCUS CONTROL

BACKGROUND OF THE INVENTION

This invention relates to an apparatus and method for testing human ability to control the focus of an eye. The invention has particular utility in connection with the prescription of intraocular of multifocal contact lenses.

The human eye focuses on an object by flexing itself so as to bring the retina into the image plane of an object being viewed. The position of the image plane in turn depends upon the distance of the object being viewed and the focal length of the lens of the eye. As the eye ages, the focal length of the lens changes, and the image plane moves to positions which cannot be reached by the retina. Prescription lenses compensate by shifting the position of the image plane. As the aging process continues, the eye muscles lose their flexing ability and eventually deteriorate to the point where they cannot accommodate the range of image plane positions associated with near and far objects. It then becomes necessary to provide multifocal length corrective lenses. Whether a multifocal lens is of the conventional type or the contact type, the focal length varies in an angular pattern expected to correspond to the variation of object distances.

The person who wears a conventional multifocal corrective lens tilts his head so as to position the lens at an angle which places the correct focal length region thereof along the optical axis between the eye and the object. The eye rotates in the opposite direction and then flexes that amount which will bring the retina into the image plane of the object.

A different situation obtains for the eye which is fitted with a multifocal contact lens. Here the lens moves with the eye, and creates situations wherein different images present in the instantaneous field of view may be focussed at different image planes. In this situation the eye cannot be flexed so as to bring both images into simultaneous perfect focus. Consequently, the brain must select one image or the other and control the eye muscles to bring that image into focus. This requires a special skill which is not well developed in some persons. Heretofore there has been no test for this skill. Indeed there has been no appreciation of the need to perform such a test. The practitioner has measured and tested the eye with a view toward obtaining the correct physical fit and the proper focal length range. Cognitive skills have been neglected, and therefore it has sometimes happened that the patient has developed a physiological reaction in the form of headaches or blurred vision. This has occurred after the lens has been worn for a period of time, and it cannot be corrected by a change of prescription.

It has been found in accordance with the practice of this invention that it is practical to test the cognitive skill related to focus control. It is believed that the results of such a test provide an indication of adaptability to contact lenses. It is also believed that the focus control skill may be impaired by a variety of physiological conditions and that an effective test of that particular skill may provide a valuable diagnostic tool.

SUMMARY OF THE INVENTION

This invention provides apparatus and method for testing human ability to select among focally conflicting images and to focus upon the image which is selected. An optical arrangement is provided for creating bundles of light rays representing two different objects at two apparently different distances and directing the light ray bundles along a common optical axis for viewing by a human eye located at a viewing position therealong. Preferably, the two light ray bundles are generated within a viewing box having a peephole at the desired viewing position. Two distinctively different targets are illuminated and the illuminating light is reflected as light ray bundles along two different paths. The light ray bundles are directed so as to merge along a common axis. The viewing box is provided with optical means which cause the two light ray bundles to have different convergences, so than they appear to have originated at targets located at different distances from the peephole. After passing through the lens of the eye, the two light ray bundles become focused at image planes located at different axial positions.

When the eye of a test subject is positioned at the peephole, two different, focally conflicting, images are presented. Preferably the viewing box is provided with optics which are selected to present images at two apparent distances corresponding to the maximum accommodation range of the eye. Consequently the eye is able to focus upon either object, but not both at the same time. It has been found that some persons are able to focus upon either of the two images and to shift back and forth upon command. Others can do this only with difficulty and may experience uncontrolled switching. It is believed that persons in this latter category are not good candidates for multifocal contact lenses.

DESCRIPTION OF THE PREFERRED EMBODIMENT

Figure 1:
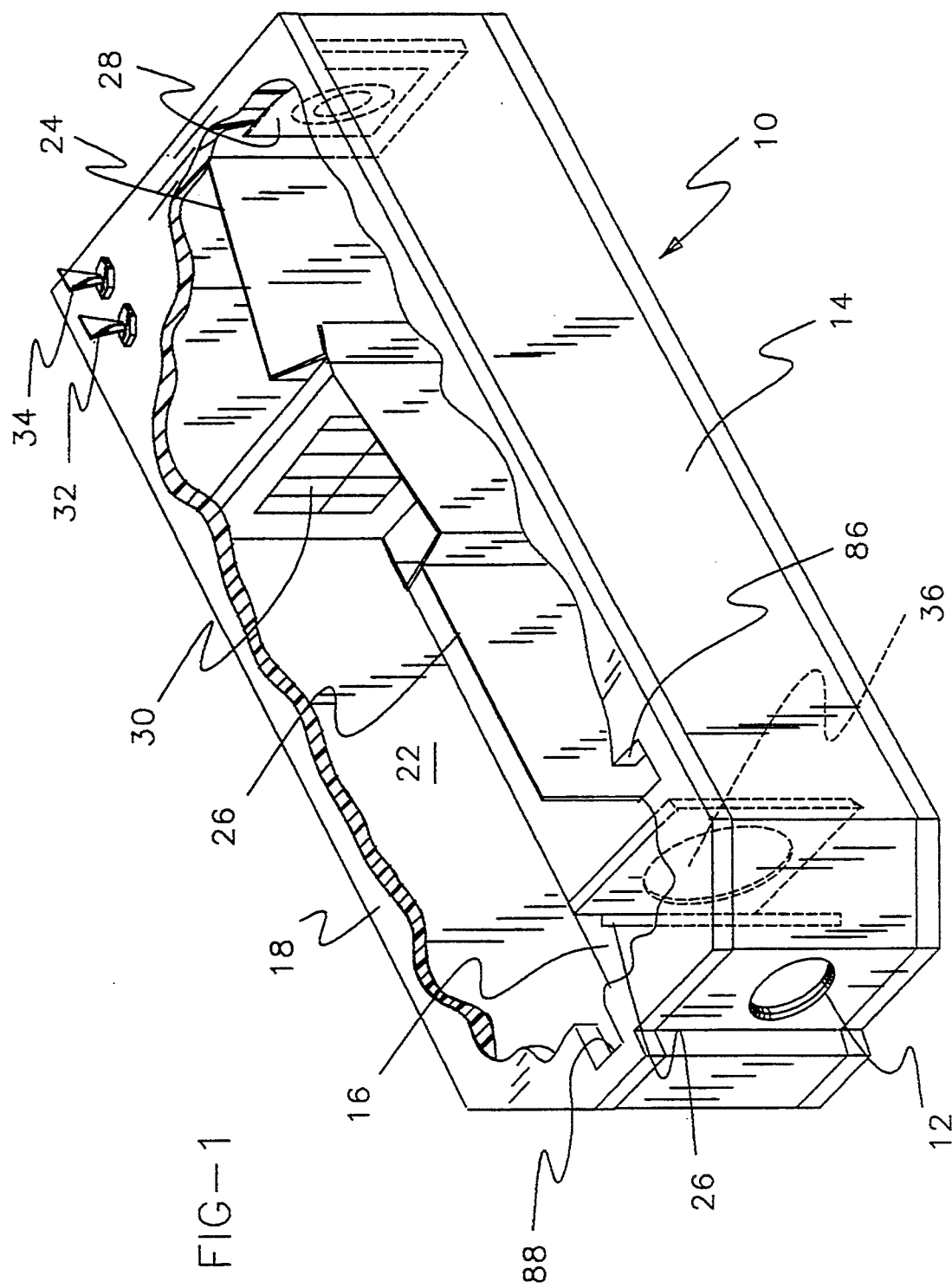
FIG. 1 is a partially cut-away perspective view of a viewing box according to the invention.

A viewing box 10 for use in practicing the invention is illustrated in FIG. 1 with the top wall 18 partially cut away for illustration of the interior components. Viewing box 10 may comprise, in addition to top wall 18, suitably configured side walls 14 and a bottom wall 16. A distinctive "distant" target such as a bull's-eye 28 may be positioned directly opposite an aperture or peephole 12. A distinctively different "near" target such as a vertical line display 30 is positioned in viewing box 10 alongside target 28 with baffles 22,24 and partition 20 therebetween. A pair of light switches 32,34 may be positioned on top wall 18. A pair of dimmer control knobs (illustrated schematically as variable resistors 90,92 in FIG. 5) may also be provided.

Figure 2:
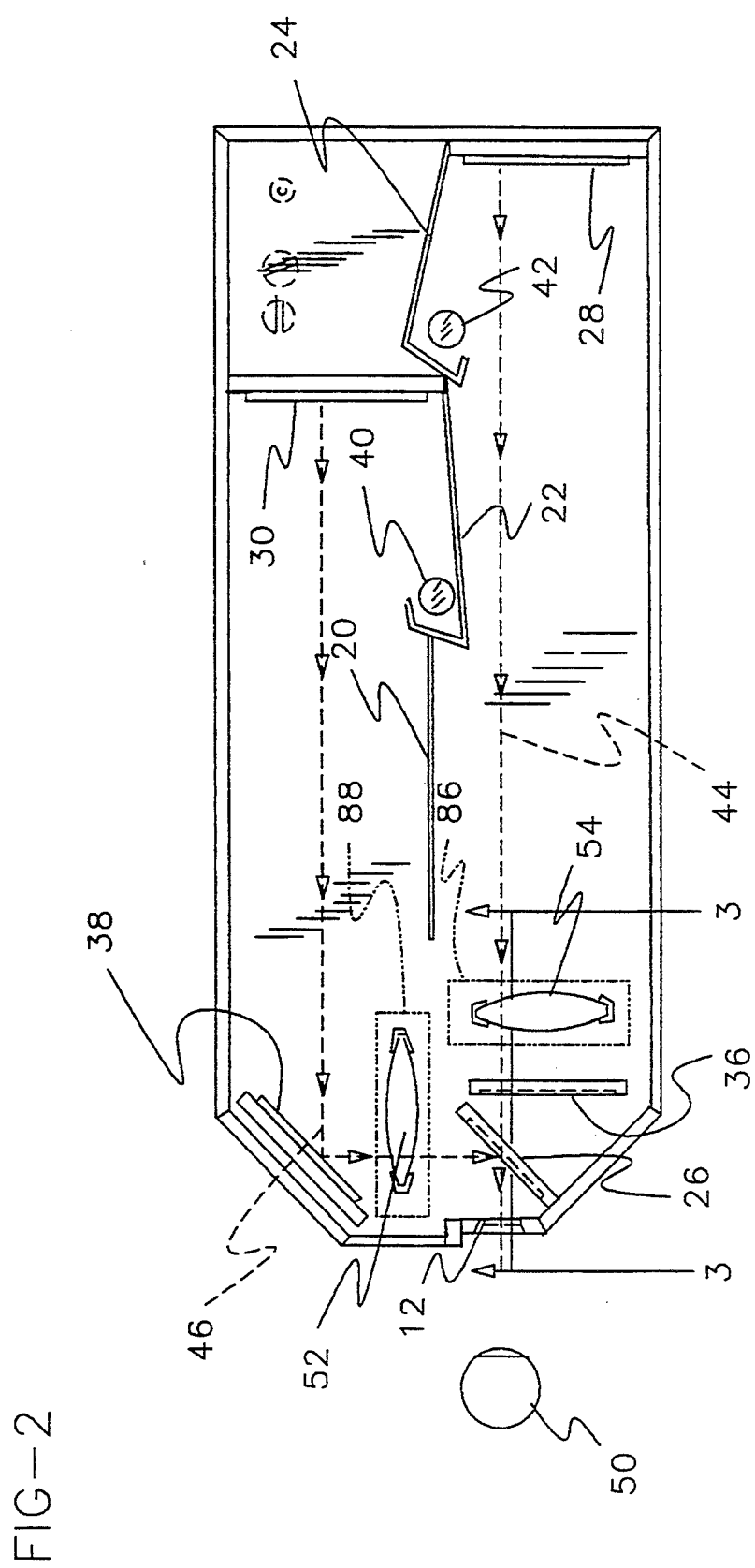
FIG. 2 is a cut-away top elevation view of the viewing box.

When targets 28,30 are illuminated, they reflect light ray bundles along optical paths 44,46 respectively, as illustrated in FIG. 2. Suitable illumination may be provided by lamps 42,40 shrouded by baffles 24,22 respectively.

Figure 3:
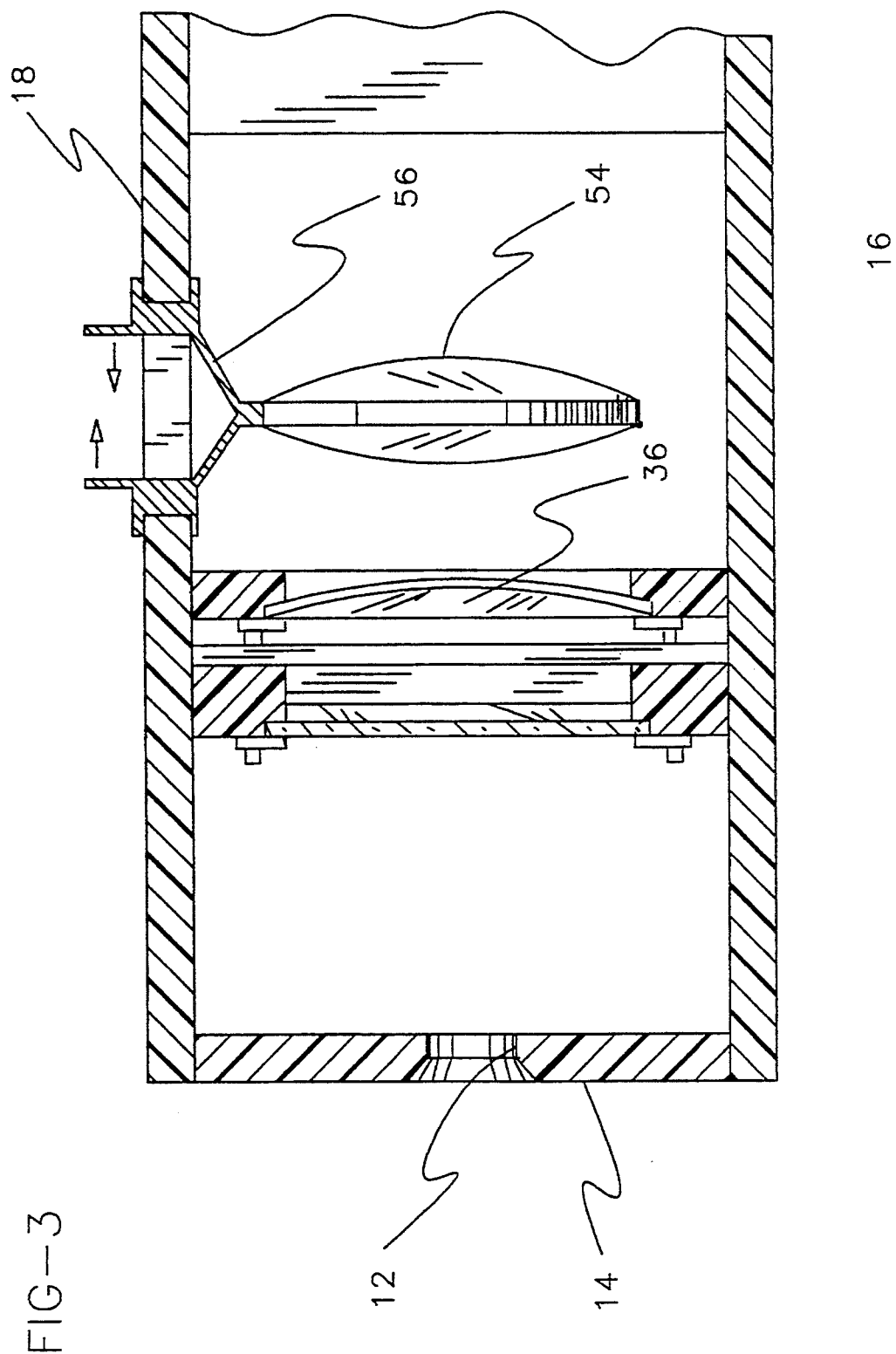
FIG. 3 is an enlarged cross-sectional view taken along lines 3—3 of FIG. 2.

Optical path 44 passes through an objective lens 36 which is illustrated in detail in FIG. 3. Lens 36 may be a positive meniscus lens having a power of about three diopters. For a viewing box of convenient size, such a lens will fairly well collimate the light ray bundle traveling along optical path 44, thereby making target 28 appear to be at a very great distance.

After passing through lens 36, light rays traveling along optical path 44 pass through a beam splitter 26. Beam splitter 26 may be a half silvered mirror as illustrated, but a prism may be provided as a suitable alternative. In either event the light rays follow an optical axis which passes through the peephole 12 and into the eye 50 of an observer.

Light rays reflected from the target 30 travel along a path 46 which is initially parallel to, but offset from, optical path 44. These light rays are directed toward a front surface mirror 38 and are reflected perpendicularly toward beam splitter 26. These light rays are reflected a second time by beam splitter 26 and are merged into the optical axis passing through peephole 12. Thus a far object and a near object are presented to the eye at the same time.

As a preliminary step, the eye is examined to determine appropriate prescription lenses for far and near viewing. Corrective lenses 54,52 having the required focal lengths for distance vision and near vision respectively, (and any needed cylinder correction) are inserted through slots 86,88 of top wall 18 and suspended in space by a suitable means such as, for instance, a spring clip 56 of the type shown in FIG. 3. With corrective lenses 54,52 in place, the eye 50 is able to see both targets, at least non-simultaneously. The focal lengths of lenses 52,54 are selected for focusing targets 28,30 at image planes within the maximum accommodation ability of the eye 50.

Figure 4:
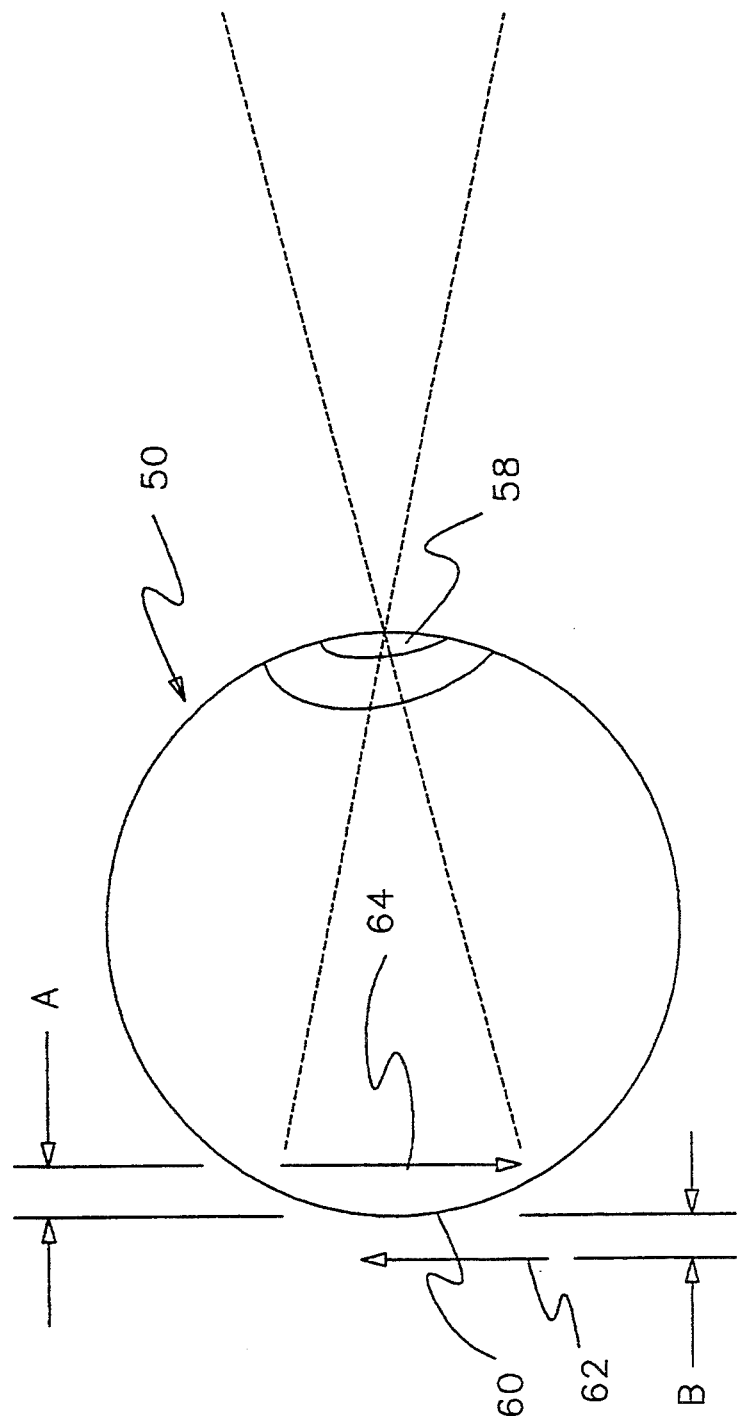
FIG. 4 is a schematic illustration of conflicting focusing requirements presented to a human eye.

The two above-mentioned image planes may be located inside the eye 50 at positions indicated by the arrows 62,64 of FIG. 4. The drawing of FIG. 4 assumes that the lens 58 of eye 50 is positioned along the optical axis 44 at peephole 12. This causes one image to be in focus at a distance A in front of retina 60, while the other image is in focus at a distance B behind the retina. Therefore the eye muscles must be able to flex the retina a total distance of A+B in order to accommodate the focusing task posed by the two image planes. It is obvious that the retina 60 cannot be put in a position such that both images are in simultaneous perfect focus. In general the brain will pick one of the two images and control the eye muscles to move the retina into the image plane of that image. However, it is possible to shift images by concentrating on the image which is out of focus. Some persons are able to focus upon either image at will; others cannot. Where the image shifting ability exists, it seems to be affected by the relative illumination of the two targets. Thus the ability can be measured quantatively by testing switching success under a variety of relative lighting conditions.

Figure 5:
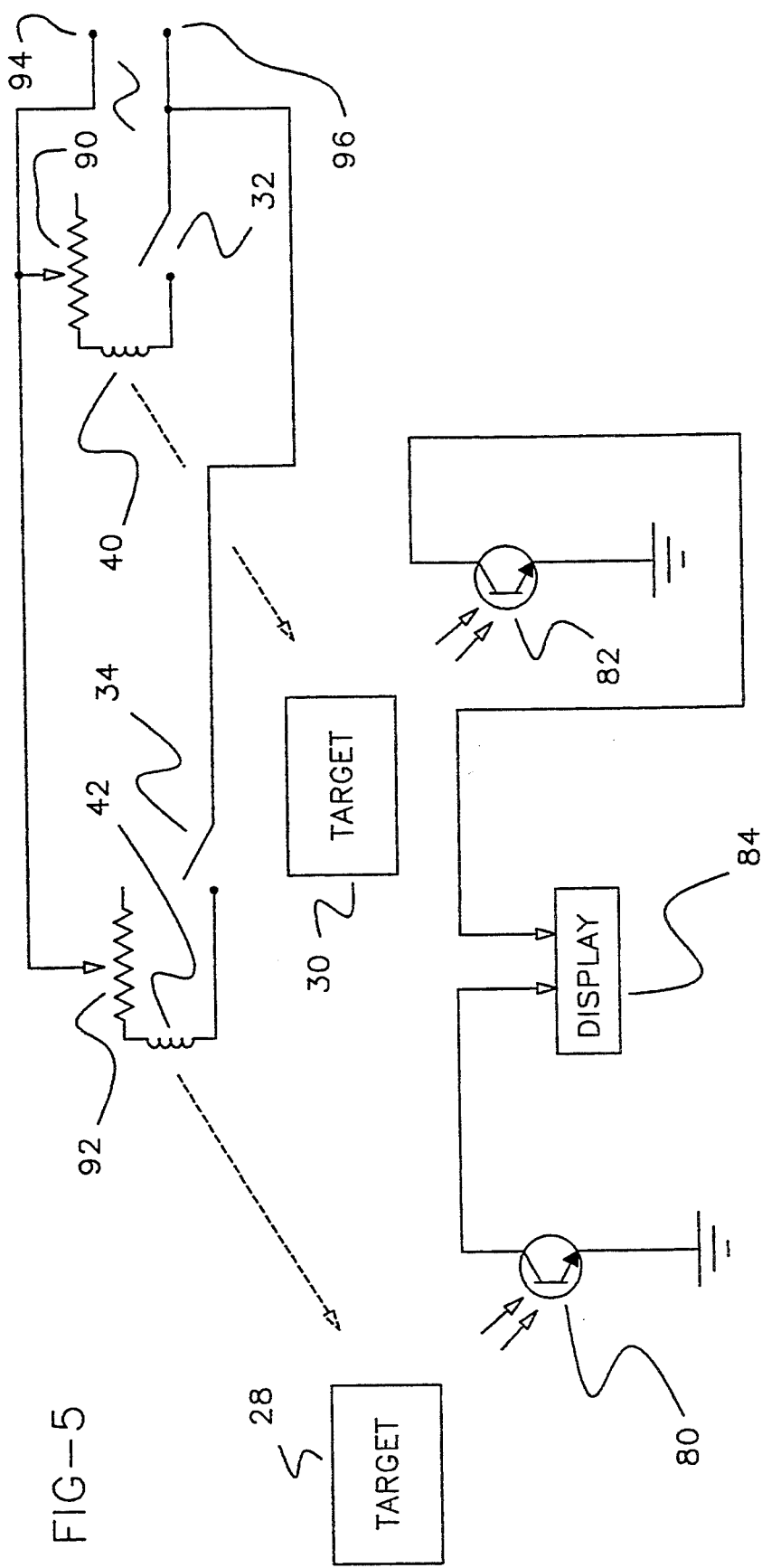
FIG. 5 is a schematic illustration of an illumination control circuit.

FIG. 5 illustrates the electrical connection of lamps 40,42. It is convenient to wire the lamps in parallel to input power terminals 94,96 through a pair of switches 32,34. Variable resistors 90,92 provide dimming control for lamps 40,42. This enables an evaluation of the effects of differential illumination upon target preference. A pair of photodetectors 80,82 may be arranged for observing the illumination levels of targets 28,30 respectively, and the output signals therefrom may be supplied to a display 84.

In operation, switches 32,34 are alternately closed to enable the subject to see each of targets 28,30 separately. Initially, dimmer controls 90,92 are adjusted for optimum viewing of each of the targets. Thereafter, both of switches 32,34 are closed, and the subject is asked to report regarding target being seen. Then the subject is directed to focus on the other target. The process is repeated for a variety of settings of dimmer controls 90,92. The test is considered favorable, if the subject is able to switch between targets over the full range of focus accommodation. The test results are considered to be particularly favorable, if the subject is able to make such a switch from a brightly illuminated target to a dimly illuminated target.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. Apparatus for testing visual focus control ability comprising:

location reference means for positioning an eye of an observer so as to place the retina thereof at a predetermined position;

first imaging means for projecting a first image along an optical axis directed into said eye, for focussing at a first image plane situated in axial proximity to said predetermined position; and second imaging means for projecting a second image along said optical axis concurrently with the projection of said first image for focussing at a second image plane situated in axial proximity to said predetermined position and axially displaced from said first image plane, so that simultaneously conflicting focussing demands are established for an eye positioned as aforesaid.

2. Apparatus according to claim 1 wherein said second imaging means comprises means for projecting said second image along an optical path having a point of intersection with said optical axis, and a beam splitter positioned at said point of intersection for redirecting said second image along said optical axis.

3. Apparatus for testing the ability of an eye to switch between focally conflicting images comprising:

a generally enclosed viewing box provided with a bottom wall, a top wall, side walls and a peephole in one of said walls;

a first target having a distinctive appearance and mounted inside said viewing box for viewing by an eye positioned near said peephole;

a second target having a distinctive appearance different from said first target and mounted inside said viewing box for viewing by an eye positioned near said peephole;

illumination means mounted inside said viewing box for simultaneously illuminating said first and second targets;

an objective lens mounted inside said viewing box for adjusting an apparent distance of said first target from said peephole to be substantially different from that of said second target; and reflection means mounted inside said viewing box for presenting simultaneous, coaxial, but focally conflicting, views of said first target and said second target by an eye positioned near said peephole.

4. Apparatus according to claim 3 further comprising first and second corrective lenses mounted inside said viewing box for adjusting the axial positions of image planes presented by said first target and said second target to an eye positioned as aforesaid.

5. Apparatus according to claim 4 and further comprising means for differentially controlling the illumination of said targets.

6. Apparatus according to claim 5 and further comprising means for sensing the illumination level of each of said targets and means for creating a visual display indicative of the illumination levels so sensed.

7. A method of testing the focal control ability of a subject person comprising the steps of:
   (1) creating a first bundle of light rays defining a first image;
   (2) directing said first bundle of light rays along an optical axis toward a viewing point and with a convergence such that said image appears to originate from an object at a first distance from said viewing point;
   (3) creating a second bundle of light rays defining a second image distinctively different from said first image;
   (4) directing said second bundle of light rays along said optical axis toward said viewing point and with a convergence such that said second image appears to originate from an object at a second distance from said viewing point, said second distance being different from said first distance and said second bundle of light rays arriving at said viewing point substantially simultaneously with said first bundle of light rays;
   (5) instructing said person to position an eye at said viewing point and focus upon one of said images; and
   (6) instructing said person to focus upon the other of said images.

8. A method according to claim 7 and further comprising the steps of adjusting the relative intensities of said first and second light ray bundles; said method then being repeated for the adjusted light ray bundles.

* * * * *